US006908742B2

(12) United States Patent
Neely

(10) Patent No.: US 6,908,742 B2
(45) Date of Patent: *Jun. 21, 2005

(54) METHODS AND KITS FOR THE DETECTION OF ENDOTOXIN

(75) Inventor: Constance F. Neely, Raleigh, NC (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 55 days.

This patent is subject to a terminal disclaimer.

(21) Appl. No.: 10/137,004

(22) Filed: Jun. 12, 2002

(65) Prior Publication Data

US 2002/0182641 A1 Dec. 5, 2002

Related U.S. Application Data

(63) Continuation of application No. 09/180,110, filed as application No. PCT/US97/08754 on May 23, 1997, now abandoned, which is a continuation of application No. 08/652,928, filed on May 24, 1996, now Pat. No. 5,773,306.

(51) Int. Cl.[7] ...................... G01N 33/53; G01N 33/537; G01N 33/543

(52) U.S. Cl. ...................... 435/7.93; 435/7.8; 435/7.21; 436/518

(58) Field of Search ........................... 435/7.93, 7.8, 435/7.21, 7.1, 7.92, 7.94, 7.95; 436/518, 501, 543, 63

(56) References Cited

U.S. PATENT DOCUMENTS 5,773,306 A * 6/1998 Neely

OTHER PUBLICATIONS

Nagata, Y. and Shirakawa, K., "Seating standards for the levels of endotoxin in the embryo culture media of human *in vitro* fertilization and embryo transfer", *Fertility and Sterility*, 1996.
Akarasereenont et al., "Comparison of the induction of cycloooxygenase and nitric oxide synthase by endotoxin in endothelial cells and macrophages", *Eur. J. Pharmacol.* 1995.
Brigham et al., "Endotoxin and Lung Injury", *Am. Rev. Respir. Dis.* 1986, 133:913–927.
Bruns, R.F. "Adenosine Receptor Binding Assays", *Receptor Biochemistry and Methodology, vol. II: Adenosine Receptors*, DMF Cooper and C. Londos (eds), Alan Liss, Inc., New York, NY, 1988, pp 43–62.
Kambayashi et al., "A novel endotoxin–specific assay by turbidimetry with *Limulus* amoebocyte lysate containing β–glucan",*J. Biochem. Biophys. Methods* 1991, 22:93–100.
Ku, H–H, et al., "Monoclonal Antibodies to Adenosine Receptor by an Auto–Anti–Idiotypic Approach", *J. Immunol.* 1987 139:2376–2384.

Jacobson et al., "Adenosine Receiptors: Pharmacology, Structure–Activity Relationships, and Therapeutic Potential", *J. Med. Chem.* 1992, 35:407–422.
"Increase in National Hospital Discharge Survery Rates for Septicemia—United States, 1979–1987", *MMWR* 1990, 39:31–34.
Minobe et al., "Assay of Endotoxin in Human Plasma Using Immobilized Histidine, *Limulus* Amoebocyte Lysate and Chromogenic Substrate",*Eur. J. Clin. Chem. Clin. Biochem.* 1994, 32:797–803.
Morita et al., "A New (1–3)β–D–Glucan–Mediated Coagulation Pathway Found in *Limulus* Amebocytes", *FEBS Letters* 1981 129:318–321.
Morrison, "Endotoxins and Disease Mechanisms", *Ann. Rev. Med.* 1987, 38:417–432.
Obayashi et al., "A new chromogenic endotoxin–specific assay using recombined limulus coagulation enzymes and its clinical applications", *Clinica Chimica Acta* 1985, 149:55–65.
Obayashi, T. J., "Addition of perchloric acid to blood samples for colorimetric limulus test using chromogenic substrate: Comparison with conventional procedures and clinical applications", *Lab. Clin.*
Nawata et al., "Specific assay for endotoxin using immobilized histidine, *Limulus* amoebocyte lysate and a chromogenic substrate", *J. Chromatography* 1992, 597:415–424.
Pfeiffer, M. and Weiss, A.R, "Removal of Lal–test interfering low molecular weight substances by ultrafiltration", *Detection of Bacterial Endotoxin with the Limulus Amebocyte Lysate Test*, WW.
Rietschel et al., "Bacterial endotoxin: molecular relationships of structure to activity and function", *FASEB J.* 1994, 8:217–225.
Schletter et al., "Molecular mechanisms of endotoxin activity", *Arch. Microbiol.* 1995, 164:383–389.
Thomas et al., "Quantitative endotoxin determination in blood with a chromogenic substrate", *Clinica Chimica Acta*. 1981, 116:63–68.
Wessels et al., "Plasma endotoxin concentration in healthy primates and during *E. coli*–induced shock", *Crit. Care Med.* 1988 16:601–605.
Williams et al., "Ketoconazole inhibits alveolar macrophage production of inflammatory mediators involved in acute lung injury (adult respiratory distress syndrome)", *Surgery* 1992, 112:270–277.
Wright, "Multiple receptors for endotoxin", *Current Opinion in Immunol.* 1991, 83–91.
Zhang et al., "Sensitive Quantitation of Endotoxin by Enzyme–Linked Immunosorbent Assay with Monoclonal Antibody against *Limulus* Peptide C", *J. Clin. Microbiol.* 1994, 32:416–422.

* cited by examiner

Primary Examiner—Patricia A. Duffy
(74) Attorney, Agent, or Firm—Licata & Tyrrell P.C.

(57) ABSTRACT

Methods for determining levels of endotoxin in a sample are provided. These methods are useful in the diagnosis of septicemia. Kits for the detection of endotoxin are also provided.

4 Claims, 5 Drawing Sheets

METHODS AND KITS FOR THE DETECTION OF ENDOTOXIN

This application is a continuation of U.S. patent application Ser. No. 09/180,110, filed Nov. 4, 1998 now abandoned, which is the National Stage of International Application No. PCT/US97/08754, filed May 23, 1997, which is continuation of U.S. patent application Ser. No. 08/652,928, filed May 24, 1996, issued as U.S. Pat. No. 5,773,306.

BACKGROUND OF THE INVENTION

Septicemia is the thirteenth leading cause of death in humans, accounting for up to 100,000 deaths and $5 to $10 billion of health care expenditures annually in the United States, alone (Increase in National Hospital Discharge Survey rates for septicemia—United States, 1979–1987 *MMWR* 1990, 39:31–34; Skelter et al. *Arch. Microbiol.* 1995, 164:383–389). It is the most common cause of death in medical and surgical intensive care units, and is associated with a mortality rate of 40 to 90%.

Septicemia is caused by the release of endotoxin, also referred to herein as lipopolysaccharide (LPS), from the outer wall of gram negative bacteria into the blood stream. LPS or endotoxin is released from the outer membrane of the bacteria when they multiply, die, or lyse (Rietschel et al. *FASEB J.* 1994, 8:217–225). Following its release, this toxin produces a cascade of complex events which ultimately results in organ failure, irreversible shock and death. By binding to cell membrane proteins or specific cell membrane receptors, LPS acts on a number of different cell types, including endothelial cells, neutrophils, monocytes and macrophages to induce the release of a number of mediators, including oxygen free radicals, nitric oxide, metabolites of arachidonic acid, thromboxane, prostacyclin, and platelet activating factor, chemoattractants, interleukin (IL)-8 and leukotriene B4, cytokines, IL-1, tumor necrosis factor (TNF-$\alpha$), and proteases which are important in the pathophysiology of endotoxin induced organ injury and septic shock (Akarasereenont et al. *Eur. J. Pharmacol.* 1995, 273:121–128; Brigham et al. *Am. Rev. Respir. Dis.* 1986, 133:913–927; Morrison *Ann. Rev. Med.* 1987, 38:417–432; Williams et al. *Surgery* 1992, 112:270–277; Wright *Current Opinion in Immunol.* 1991, 83–91).

Despite the prevalence and severity of this disease, rapid diagnosis at an early stage is still difficult. The diagnosis of septicemia is currently based upon on clinical signs and symptoms, including clinically significant hypotension (systolic blood pressure $\leq 90$ mmHg) with suspected presence of infection, fever or hypothermia, tachycardia, tachypnea, lactic acidosis, white blood cell count >12,000 or <4,000, with or without positive blood cultures. However, by the time such clinical signs and symptoms manifest, irreversible organ and tissue damage may have already occurred. Further, results from blood cultures require at least 24 hours and do not always provide a definitive diagnosis since only 35% of patients with septicemia have positive blood cultures.

The only tests currently available for detection of endotoxin in biological fluids, or pharmacological and industrial solutions and products, are based on the availability of lysates of amebocytes isolated from the hemolymph of *Limulus* and *Tachypleus* (rare horseshoe crabs). The *Limulus* amebocyte lysate (LAL) test is based on the ability of endotoxin to coagulate with amebocyte lysate. These amebocytes have a coagulation system believed to be a prototype of mammalian blood coagulation that involves the sequential activation of proenzymes (Zhang et al. *J. Clin. Microbiol* 1994 32:416–422). Endotoxin activates the initial enzyme (factor C) of the LAL coagulation system leading to conversion of coagulogen, a clottable protein, into coagulin and peptide C. Visible formation of a gel clot indicates endotoxin activation of LAL and serves as the basis for the gel-clot method for detection of endotoxin. However, this particular method is not quantitative. In order to make this assay quantitative, a turbidimetric kinetic assay which uses a toxinometer was developed (Kambayashi et al. *J. Biochem. Biophys. Methods* 1991, 22:93–100). In addition, a chromogenic substrate for the clotting enzyme was developed (Thomas et al. *Clinica Chimica Acta.* 1981, 116:63–68). The addition of this chromogenic substrate to the assay increased the sensitivity of the LAL assay 10 to 100 times greater than that of the gel-clot method. A spectrophotometric, calorimetric (toxicolor) assay was developed by addition of a dye, N-(-1 naphthyl)-ethylenediamine, to the chromogenic substrate assay, (Minobe et al. *Eur. J. Clin. Chem. Clin. Biochem.* 1991, 32:797–803).

However, the LAL test is not sufficiently specific enough for clinical diagnosis of septicemia in human plasma. LAL tests are affected by $\beta$-glucans, $\beta$-glucan-mycotic containing reactive products, and rinses from cellulose-based dialyzers (Morita et al. *FEBS Letters* 1981 129:318–321). Further, substances in human blood having nonspecific amidolytic activities, such as factor Xa, thrombin, and trypsin act directly on the chromogenic substrate (Obayashi *J. Lab. Clin. Med.* 1984, 104:321–330) and produce false positive results. Inhibitors such as $\alpha$2-plasmin inhibitor, antithrombin III, and $\alpha$1-antitrypsin produce false negative results (Obayashi et al. *Clinica Chimica Acta* 1985, 149:55–65). Moreover, the LAL test is inhibited or enhanced by many substances including antibiotics, hormones, heavy metals, amino acids, alkaloids, carbohydrates, plasma proteins, enzymes, and electrolytes in the sample solution (Pfeiffer, M. and Weiss, A. R, "Removal of Lal-test interfering low molecular weight substances by ultrafiltration", *Detection of Bacterial Endotoxin with the Limulus Amebocyte Lysate Test*, W W Levin and J T Novitsky (eds), Alan R. Liss, Inc., New York, N.Y., 1987, pp. 251–262). To remove such interfering substances, methods for treatment of plasma samples, with heating and dilution, perchloric acid, chloroform, ether, acid, alkali, detergents, or ultrafiltration have been tested (Pfeiffer, M. and Weiss, A. R. supra; Obayashi, T. *J. Lab. Clin. Med.* 1984, 104:321–330). However, dilution of the sample results in dilution of the endotoxin level and reduces the sensitivity of detecting low levels of endotoxin in the sample. Attempts at ultrafiltration to remove high molecular weight interfering substances have also proved unsuccessful because the pore size is too small and endotoxin may be adsorbed on the ultrafiltration membrane (Nawata et al. *J. Chromatography* 1992, 597:415–424).

Minobe et al. developed a method for eliminating interfering substances in the sample solution by adsorbing endotoxin onto immobilized histidine subsequently assayed with the LAL chromogenic substrate and toxinometer or toxicolor test (Minobe et al. *Eur. J. Clin. Chem. Clin. Biochem.* 1994, 32:797–803). However, binding of endotoxin to immobilized histidine can be affected by globulins and transferrin in human plasma which bind to endotoxin. Further, the histidine mobilization method is dependent upon the reaction time and dilution of the sample to increase the sensitivity of the measurement.

LAL enzyme-linked immunosorbent assays (ELISA) for the detection of endotoxin have also been developed with coagulogen and *Limulus* peptide C (Zhang et al. *J. Clin. Microbiol.* 1994, 32:416–422). However, these ELISAs are also affected by substances in human blood which activate or inhibit LAL as described above and like other LAL assays depend on the availability of the rare horseshoe crabs which are diminishing in populations.

Accordingly, there exists a need for a quick and reliable assay for the determination of endotoxin in a sample.

OBJECTS OF THE INVENTION

An object of the present invention is to provide methods for the determination of endotoxin levels in a sample. In one embodiment, the method comprises binding an $A_1$ adenosine receptor agent to $A_1$ adenosine receptors, contacting the bound agent and $A_1$ adenosine receptors with the sample so that any endotoxin in the sample displaces the bound agent by binding to the $A_1$ adenosine receptors, and determining an amount of displaced agent. In another embodiment, the method comprises coating a solid phase support with a first binding partner capable of immobilizing endotoxin to the solid phase support, contacting the solid phase support with a sample suspected of containing endotoxin, and contacting the solid phase support with a means for detecting endotoxin immobilized to the solid phase support. These methods are useful in diagnosing septicemia in an animal.

Another object of the present invention is to provide kits for the detection of endotoxin and diagnosis of septicemia in animals.

DETAILED DESCRIPTION OF THE INVENTION

Figure 1:
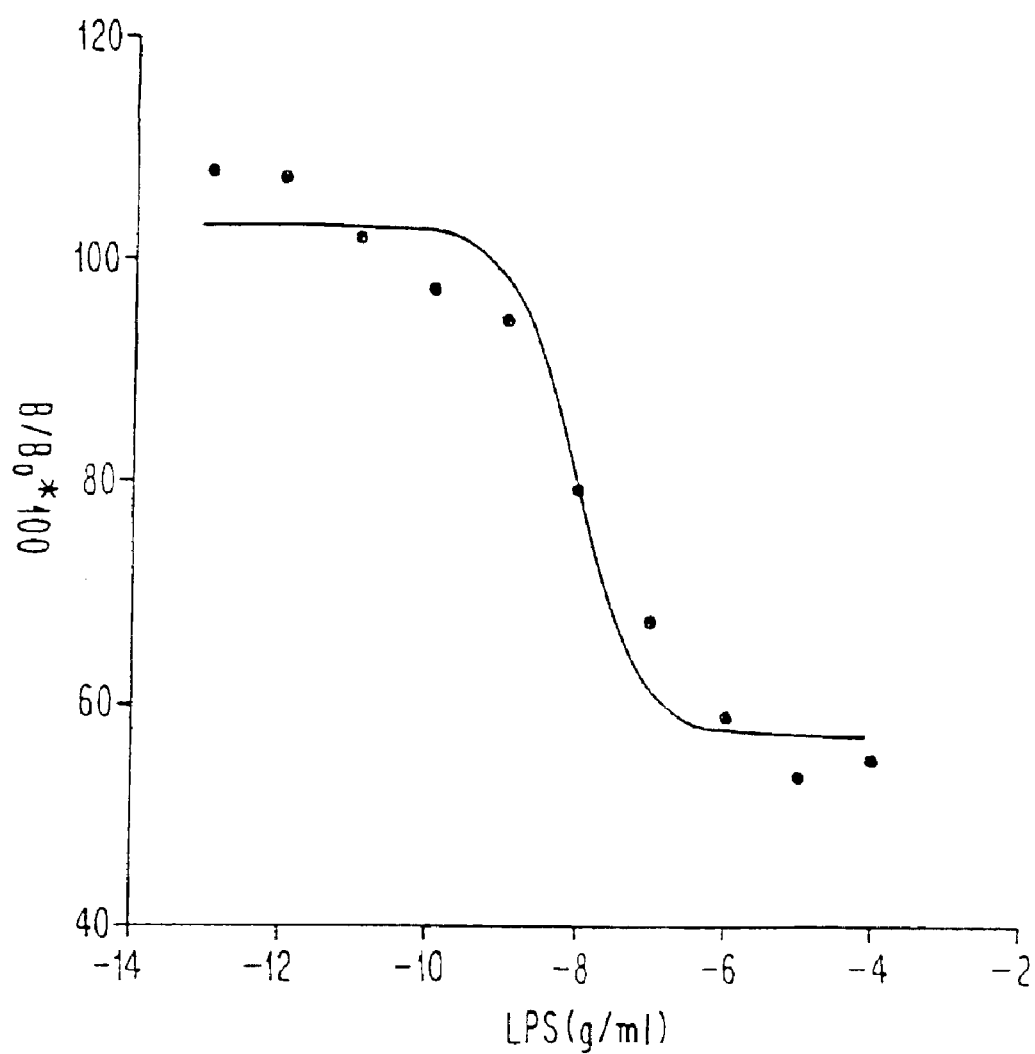
FIG. 1 shows displacement of [$^3$H] DPCPX from $A_1$ adenosine receptors in sheep brain membranes by LPS from *E. coli* 0111:B4. Competition experiments with LPS 0111:B4 (0.1 pg/ml–100 µg/ml) for [$^3$H] DPCPX (0.5 nM) were performed in duplicate.

Septicemia is a world-wide health problem which results in an enormous financial burden on the health care system and leads to death in almost half of infected individuals. The rate of septicemia in the United States increased by over 100% in the last decade. Septicemia is associated with infections with gram negative bacteria which release endotoxin. In addition, contamination of embryo culture media with endotoxin is associated with low pregnancy and birth rates following in vitro fertilization (Nagata, Y. and Shirakawa, K. *Fertility and Sterility* 1996, 65:614–619). Embryo development and fetal heart rate were not detected with endotoxin levels >2 pg/ml in the embryo culture media. Contamination of organ baths with endotoxin containing organs for transplant is believed to contribute to the failure of organ function and rejection of the transplant following transplant surgery. Contamination of pharmaceutical or industrial solutions with endotoxin has been associated with increased morbidity, mortality and their associated costs. Accordingly, an assay for endotoxin that is sensitive, specific, reproducible, and easy to perform within a short period of time is required.

It has now been found that endotoxin, also referred to as LPS, binds to and activates $A_1$ adenosine receptors. A method has now been developed for the accurate and reliable detection of endotoxin in a sample which comprises measurement of the displacement of an agent bound to $A_1$ adenosine receptors by endotoxin in a sample. Agents which bind to $A_1$ adenosine receptors are well known to those of skill in the art. Both agonists and antagonists have been synthesized for $A_1$ adenosine receptors. For example, 1,3-dipropyl-8-cyclopentylxanthine (DPCPX) is a highly selective $A_1$ adenosine receptor antagonist with negligible non-specific binding (less than 1%) in tissues (Jacobson et al. *J. Med. Chem.* 1992, 35:407–422; Bruns, R. F. "Adenosine Receptor Binding Assays", *Receptor Biochemistry and Methodology, Volume II: Adenosine Receptors*, DMF Cooper and C. Londos (eds), Alan Liss, Inc., New York, N.Y., 1988, pp 43–62). Other examples of antagonists include, but are not limited to, xanthine amine congener (XAC); xanthine carboxylic congener (XCC); 1,3-dipropyl-xanthines such as 1,3-dipropyl-8-(3-noradamantyl) xanthine (KW 3902), 1,3-dipropyl-8-(dicyclopropylmethyl)xanthine (KF 15372), 1,3-dipropyl-8-[2-(5,6-epoxy)norbornyl]xanthine (ENX), 8-(1-aminocyclopentyl)-1,3-dipropylxanthine (IRFI 117), 1,3-dipropyl-8-(3-noradamantyl)xanthine (NAX) and 1,3-dipropyl-8-(3-oxocyclopentyl xanthine (KFM 19); 1-propyl-3-(4-amino) phenethyl)-8-cyclopentylxanthine (BW-A844U), 1,3-dipropyl-8-sulfophenylxanthine (DPSPX), cyclopentyl theophylline (CPT) and 7-[2-ethyl(2-hydroxyethyl)amino]-ethyl]-3,7-dihydro-1,3-dimethyl-8-(phenylmethyl)-1H-purine-2,6-dione (Bamifylline (BAM)); $N^6$,9-methyl adenines such as (±)-$N^6$-endonorbornan-2-yl-9-methyladenine (N-0861) and 8-(N-methylisopropyl) amino-$N^6$-(5'-endohydroxy-endonorbornyl)-9-methyladenine (WRC-0571); $N^6$,9-disubstituted adenines; 2-phenyl-7-deazaadenines such as (R)-7,8-dimethyl-2-phenyl-9-(1-phenylethyl)-7-deazaadenine; 7,8-dihydro-8-ethyl-2-(3-noradamantyl)-4-propyl-1H-imidazo[2,1-i] purin-5(4H)-one; (±)R-1-[(ε)-3[2-[phenylpyrazolo(1,5-a) pyridin-3-yl]acryloyl]-2-piperidine ethanol; 8-azaxanthines such as 7-cyclopentyl-1,3-dipropyl-8-azaxanthine; and tetrahydrobenzothiophenones such as ethyl-3-(benzylthio)-4-oxo-4,5,6,7-tetrahydrobenzo[c]thiophene-1-carboxylate. Examples of $A_1$ adenosine receptor agonists include, but are not limited to, R-$N^6$-isopropyladenosine (R-PIA); 2-chloro-$N^6$-cyclopentyladenosine (CCPA); cyclohexyladenosine (CHA); and $N^6$-(4-amino-3-benzyl)adenosine (ABA).

Measuring the displacement of these agents by LPS can be performed in accordance with various methods known to those of skill in the art. In a preferred embodiment, the agent is detectably labeled and displacement is determined by measuring displaced label. Examples of detectable labels include, but are not limited to, enzymes, fluorescent compounds, chemiluminescent compounds, bioluminescent compounds, or radionuclide. The present inventor's discovery that LPS binds to $A_1$ adenosine receptors may be used to develop enzyme linked immunoassay (ELISA) and radioimmunoassay (RIA) tests to assay for the presence of endotoxin in a sample, using principles of ELISA and RIA which are known in the art. In these assays, a solid phase support is coated with a first binding partner capable of immobilizing endotoxin to the solid phase support, or a first binding partner capable of immobilizing $A_1$ adenosine receptors to the support while leaving the $A_1$ adenosine receptors free to bind to LPS, or a first binding partner capable of immobilizing $A_1$ adenosine receptor-LPS complex or monoclonal antibodies to $A_1$ adenosine receptor-LPS complex. Examples of first binding partners include, but are not limited to, $A_1$ adenosine receptors, LPS, $A_1$ adenosine receptor-LPS complex or monoclonal antibodies to $A_1$ adenosine receptors or $A_1$ adenosine receptor-LPS complex.

A test sample suspected of containing endotoxin may be contacted directly to the solid phase support (e.g., where the solid phase support is coated with a first endotoxin binding partner), or may first be contacted with a preparation containing $A_1$ adenosine receptors and then contacted to the solid phase support (e.g., where the solid phase support contains a first binding partner capable of binding $A_1$ adenosine receptors or $A_1$ adenosine receptor-LPS complexes). Alternatively, where the solid phase support contains first binding partners capable of binding $A_1$ adenosine receptors, the solid phase support may first be contacted with a preparation of $A_1$ adenosine receptors and then contacted with the test sample. The support may be washed to remove excess unbound material when appropriate, as is known in the art.

Means for detecting endotoxin bound to the solid phase support are used to determine the presence and/or quantity of endotoxin in a test sample. By "means for detecting endotoxin" it is meant a labeled molecule which binds to the first binding partner and which is displaced therefrom by endotoxin, or binds to the first binding partner in the absence of any endotoxin bound thereto, or binds to the complex of first binding partner and endotoxin. Endotoxin detecting means are contacted with the solid phase support as is appropriate, given the particular combination of first binding partner and detecting means, based on principles known in the art. Examples of means for detecting bound endotoxin include, but are not limited to, labeled LPS, labeled $A_1$ adenosine-LPS complex, labeled monoclonal antibodies to the $A_1$ adenosine receptor, or labeled monoclonal antibodies to the $A_1$ adenosine receptor-LPS complex. The amount of endotoxin contained in a test sample can be derived by measuring the amount of labeled molecules at a given stage in the assay, as will be apparent to those skilled in the art. Examples of labels include detectable enzymes or radionuclides conjugated to the protein. Alternatively, the protein can be conjugated to a selected antigen and detected with a second antibody to the selected antigen, said second antibody being conjugated to a detectable enzyme or radionuclide. Detectable enzymes which can be used in ELISAs are well known to those of skill in the art. Examples of detectable enzymes include, but are not limited, to acetylcholinesterase, alkaline phosphatase, α-glycerophosphate dehydrogenase, asparaginase, β-galactosidase, β-V-steroid isomerase, catalase, glucoamylase, glucose oxidase, glucose-6-phosphate dehydrogenase, horse radish peroxidase, malate dehydrogenase, ribonuclease, staphylococcal nuclease, triose phosphateisomerase, urease and yeast alcohol dehydrogenase. Convenient sources of $A_1$ adenosine receptors include, but are not limited to, sheep and hamster brain. Sheep brain contains a high density of high and low affinity $A_1$ adenosine receptors (2150±165 fmol/mg) and brains from hamsters have twice the amount of $A_1$ adenosine receptors (4090±720 fmol/mg). The density of high affinity $A_1$ adenosine receptors determined using [$^3$H] CCPA is 1920±250 fmol/mg and 1630±60 fmol/mg in sheep and hamsters, respectively. Alternatively, $A_1$ adenosine receptors can be obtained from cultured feline pulmonary arterial endothelial cells (PAECS) with and without hypoxia. In addition, $A_1$ adenosine receptors can be derived from other mammalian or insect cells.

Cell lines such as Chinese hamster ovary (CHO) cells, COS-7 cells or SF9 insect cells can be transfected with cDNA from bovine, sheep, hamster, canine, rat or human $A_1$ adenosine receptors and/or treated with $A_1$ adenosine receptor promoters to increase the expression and density of $A_1$ adenosine receptors used in these assays. In one embodiment, cDNAs can be tagged with hexahistidine and FLAG (H/F) epitope to create an expression vector which can be transfected into cells by means of lipofectin or DEAE/dextran methods to increase the expression of $A_1$ adenosine receptors in tissues. Membranes of cells containing native or recombinant $A_1$ adenosine receptors are labeled with a detectable $A_1$ adenosine receptor agent. The receptors are then solubilized and purified with use of affinity chromatography and SDS polyacrylamide gel electrophoresis. Monoclonal antibodies are then raised against the purified receptors for detection of endotoxin by ELISA.

Selected antigens which can be conjugated to the means for detecting the endotoxin are well known to those of skill in the art. Examples include, but are not limited to, biotin and FITC. Methods of conjugating a selected antigen to a protein are also well known in the art. For example, LPS can be biotinylated by a number of means such as biotin-LC-hydrazide (biotinamido hexanoyl hydrazide) or biotin-LC-ASA (1-(4-azidosalicylamido-)-6-(biotinamido)-hexane and then conjugated with a detectable label such as an enzyme, fluorophore or radionuclide. The labeled, biotinylated LPS can then be used as a probe to bind and detect $A_1$ adenosine receptors in membranes prepared from different tissues or cell lines. Receptors in these membranes can then be fractionated, reduced and solubilized on two-dimensional polyacrylamide gels. Following purification, monoclonal antibodies against the LPS-$A_1$ adenosine receptor complex can be raised for detection of endotoxin by ELISA.

In the method of the present invention, an $A_1$ adenosine receptor agent is bound to $A_1$ adenosine receptors. The bound agent and $A_1$ adenosine receptors are then contacted with a sample so that any endotoxin in the sample displaces the bound agent by binding to the $A_1$ adenosine receptors. In a preferred embodiment, test samples containing any proteins such as biological samples are deproteinized by treatment with perchloric acid prior to contact. Alternatively, heating and dilution may be used in accordance with methods well known in the art. The amount of displaced agent is then measured. In a preferred embodiment, the agent is radiolabeled and the amount of displaced agent is determined by measuring radioactivity with a scintillation counter. However, as will be obvious to those of skill in the art upon this disclosure, other methods for determining the amount of displaced agent can be used. The endotoxin levels in the sample are then determined by comparison to a standard curve derived by measuring displaced agent by known concentrations of a known endotoxin.

With the use of monoclonal antibodies for purified $A_1$ adenosine receptors (Ku, H-H, et al. *J. Immunol.* 1987 139:2376–2384) or purified $A_1$ adenosine receptor-LPS complex, radioimmunoassays (RIA) and ELISAs can also be used for the detection of endotoxin. In these assays, a sample such as plasma or saline with LPS, is added to a solid phase support coated with a binding partner for endotoxin such as purified native or recombinant $A_1$ adenosine receptors, an $A_1$ adenosine receptor-LPS complex or monoclonal antibody to these. The term "solid phase support" refers to any support to which endotoxin binding partners can be attached. A preferred solid phase support used in these assays is a plastic microtiter plate. Examples of other solid phase supports which can also be used in the present invention include, but are not limited to, polystyrene beads and slides. The solid phase support is then treated with a means for detecting any bound endotoxin in the sample. Examples of such means include proteins such as monoclonal antibodies for $A_1$ adenosine receptors (MabA$_1$AR), monoclonal antibodies for an $A_1$ adenosine receptor-LPS complex, purified $A_1$ adenosine receptors, an $A_1$ adenosine receptor-LPS complex or LPS conjugated with either: a radionuclide; a detectable enzyme, i.e., horse radish peroxidase, and a substrate solution capable of detecting the enzyme, i.e., a tetramethyl benzene (TMB) or o-phenylenediamine (OPD) solution; or an antigen and a second antibody to the antigen labeled with a detectable enzyme or radionuclide. The determination of endotoxin in a sample is based upon detection of the bound enzyme or radionuclide directly or via the second antibody. Standard curves for known concentrations of endotoxin are also determined by these assays. The curves generated for test samples are compared to these standard curves for quantitating the level of endotoxin in the test sample.

By "sample" or "test sample" it is meant to include, but is not limited to, biological samples derived from an animal, such as whole blood, plasma, serum, CSF, urine, saliva, pleural fluid, peritoneal fluid (including ascites), bronchoalveolar lavage (BAL) fluid, synovial fluid, sinus fluid, and fluid from cysts; embryo culture media; organ baths; pharmaceutical solutions and products; and industrial solutions and products.

Endotoxin levels in the serum of normal healthy volunteers is less than 3 pg/ml (Obayashi et al. *Clinica Chimica Acta* 1985, 149:55–65). It has been reported that 0.5 ng/kg (7 pg/ml in a 70 kg adult) endotoxin produces granulocytosis of 200–300% within 4 hours in normal healthy volunteers (Wessels et al. *Crit. Care Med.* 1988 16:601–605). A slightly higher dose of endotoxin, 0.8 ng/kg (10 pg/ml) is pyrogenic. Levels greater than 20 pg/ml have been associated with septicemia (Zhang et al. *J. Clin. Microbiol.* 1994 32:416–422).

Accordingly, methods of the present invention can be used to diagnose septicemia in an animal. By "animal" it is meant to include, but is not limited to, mammals, fish, amphibians, reptiles, birds, marsupials, and most preferably, humans. Thus, in a preferred embodiment, a clinician can measure the levels of endotoxin in a sample from a human and rapidly and accurately diagnose septicemia. In this embodiment, a sample, preferably a plasma sample, is obtained from a human suspected of having or being at risk for septicemia. Signs or symptoms which may lead a clinician to suspect that a human has septicemia include, but are not limited to, fever or hypothermia, chills, rigors, diaphoresis, increased respiratory rate, increased heart rate, altered mental status, confusion, and lowered blood pressure in conjunction with shock. Examples of humans at risk for septicemia include, but are not limited to, those with indwelling catheters such as urinary, intravenous or endotracheal catheters, CSF drainage tubes, joint or wound drainage tubes, chest tubes, or peritoneal catheters for dialysis, and immunocompromised individuals such as those with cancer, leukemia, AIDS or other immunological disorders, diabetes, kidney disease, liver disease, and individuals being treated for cancer by chemotherapy. Endotoxin levels in a sample are then determined in accordance with a method of the present invention.

In membranes prepared from cultured feline PAECs and sheep brain, a selective $A_1$ adenosine receptor agonist, R-$N^6$-isopropyladenosine (R-PIA) displaces binding of the highly selective $A_1$ adenosine receptor antagonist radioligand, [$^3$H]-1,3-dipropyl-8-cyclopentyladenosine xanthine [$^3$H] DPCPX. In cultured feline PAECs, a selective $A_2$ adenosine receptor agonist, 2-phenylaminoadenosine (CV 1808) did not displace bound [$^3$H] DPCPX. Accordingly, the ability of endotoxin to bind to $A_1$ adenosine receptors in different tissues and species was demonstrated. LPS displaces the highly selective $A_1$ adenosine receptor antagonist ligand [$^3$H] DPCPX in a dose-dependent manner in membranes prepared from sheep and hamster brains and cultured feline PAECs (with and without hypoxia). The lowest sensitivity of the assay for LPS (in saline and plasma) is in hamster brain membranes at 100 pg/ml. Further, with the use of membranes prepared from hamster brains, serum pretreated with PCA had no effect on [$^3$H] DPCPX binding. There was no difference in the effect of blank samples (without LPS) of saline and plasma (deproteinized with PCA) on [$^3$H] DPCPX binding to hamster brain membranes. In addition, there was a 98% recovery rate of LPS (*E. coli* 0111:B4) from plasma in this binding assay using hamster brain membranes and [$^3$H] DPCPX.

The Kd (dissociation constant or receptor affinity) and Bmax (receptor density) of adenosine $A_1$ receptors for the selective $A_1$ adenosine receptor antagonist [$^3$H] DPCPX were determined in saturation experiments in both sheep and hamster brains and in feline PAECs with hypoxia and without hypoxia (also referred to herein as normoxia). Results from these experiments are shown in Table 1.

TABLE 1

Saturation Experiments with [$^3$H]-DPCPX in Membranes from Sheep and Hamster Brains and Feline PAECs

| | Bmax (fmoles/mg protein) | Kd (nM) |
|---|---|---|
| Sheep Brain | 2251 | 0.37 |
| Hamster Brain | 3733 | 0.32 |
| Cell Normoxia | 1064 | 0.33 |
| Cell Hypoxia | 1458 | 0.26 |

Figure 2:
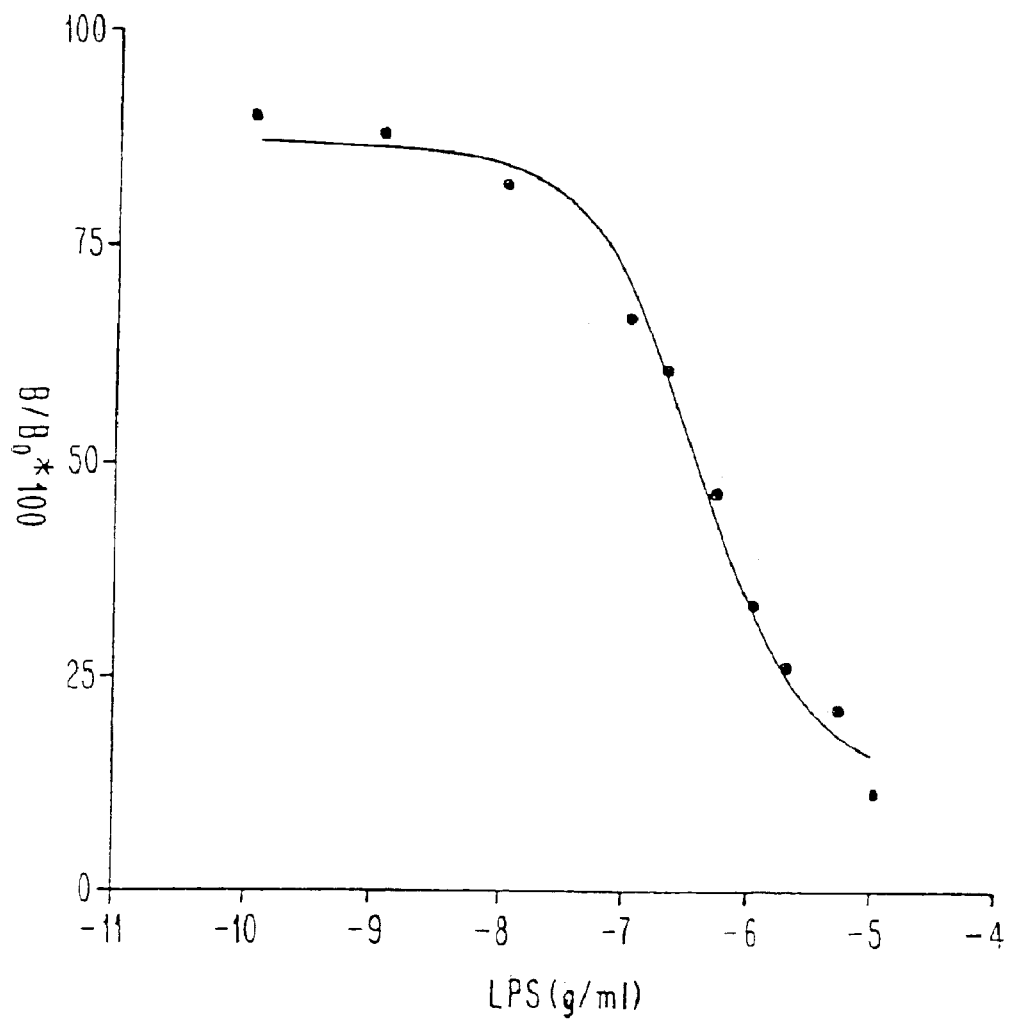
FIG. 2 shows the displacement of [$^3$H] DPCPX from $A_1$ adenosine receptors in hamster brain membranes by LPS from *E. coli* 0111:B4. Competition experiments with LPS 0111:B4 (0.1 ng/ml–10 µg/ml) for [$^3$H] DPCPX (0.5 nM) were performed in duplicate.
Figure 3:
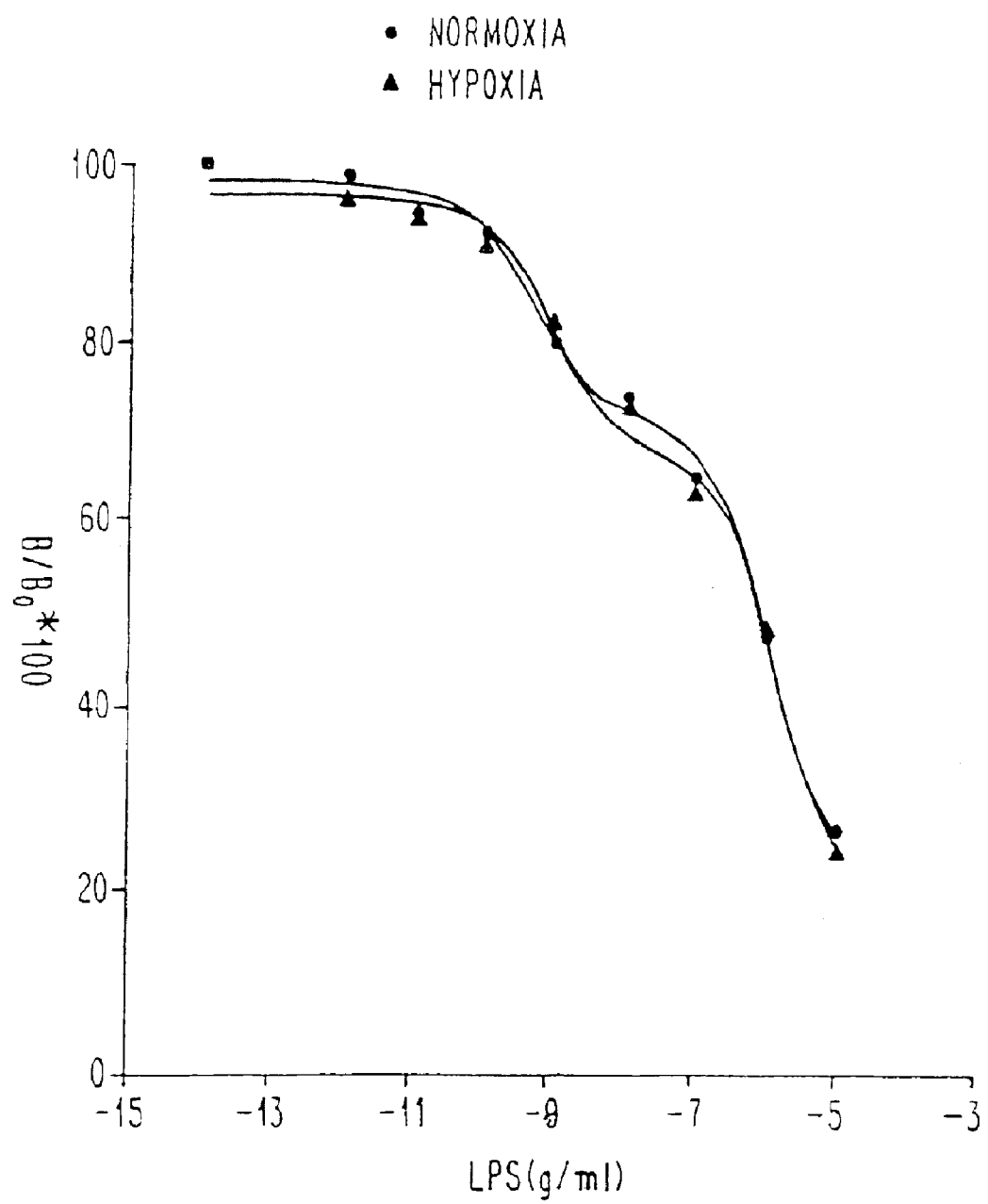
FIG. 3 shows the displacement of [$^3$H] DPCPX from $A_2$ adenosine receptors in membranes from feline PAECs with and without hypoxia by LPS from *E. coli* 0111:B4. Competition experiments with LPS 0111:B4 (0.01 pg/ml–10 µg/ml) for [$^3$H] DPCPX (0.5 nM) were performed in duplicate.
Figure 4:
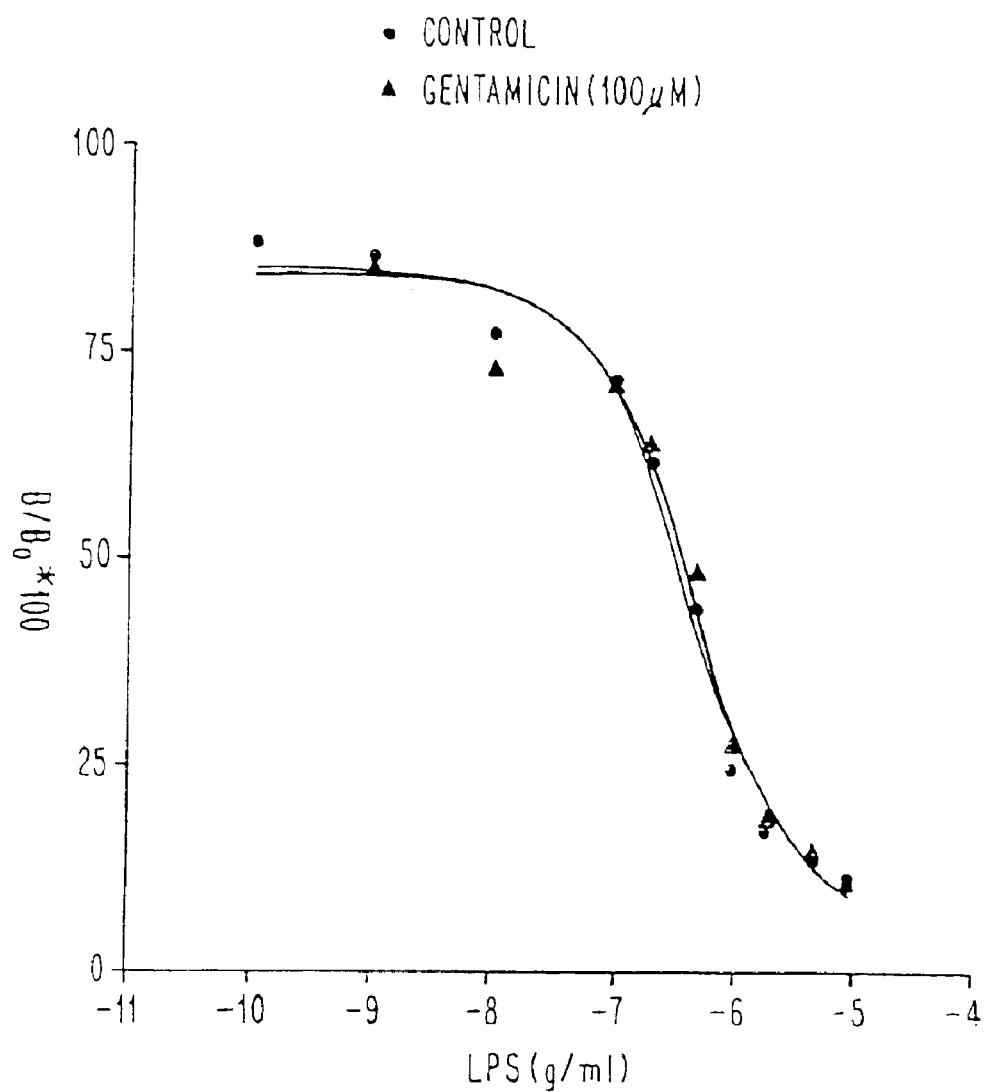
FIG. 4 shows the displacement of [$^3$H] DPCPX from $A_1$ adenosine receptors in hamster brain membranes by LPS from *E. coli* 0111:B4. Competition experiments with LPS 0111:B4 (0.1 ng/ml–10 µg/ml) for [$^3$H] DPCPX (0.5 nM) were performed in the presence of gentamicin (100 µM) in duplicate.
Figure 5:
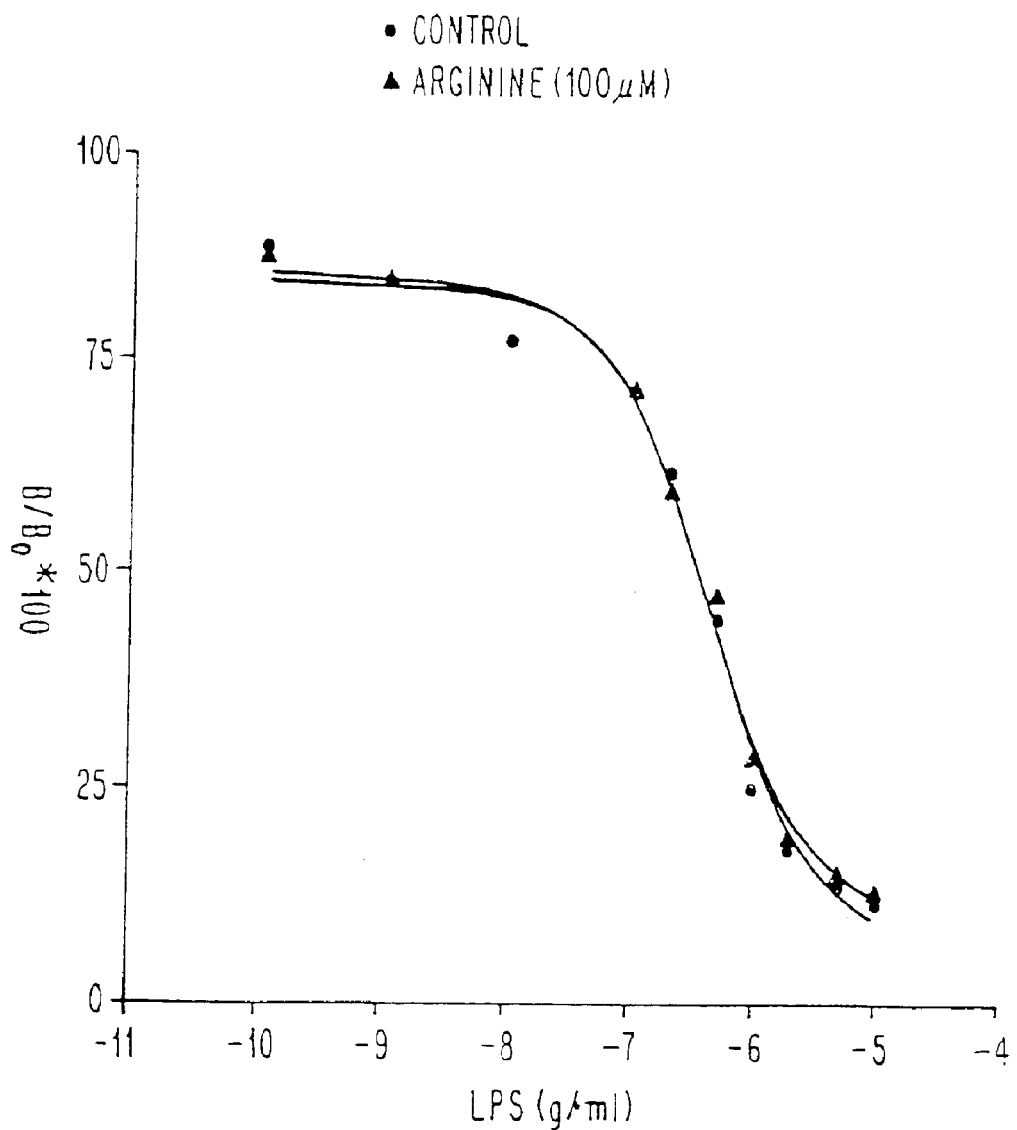
FIG. 5 shows the displacement of [$^3$H] DPCPX from $A_1$ adenosine receptors in hamster brain membranes by LPS from *E. coli* 0111:B4. Competition experiments with LPS 0111:B4 (0.1 ng/ml–10 µg/ml) for [$^3$H] DPCPX (0.5 nM) were performed in the presence of arginine (100 µM) in duplicate.

Competitive binding experiments with LPS in membranes prepared from sheep and hamster brains and feline PAECs were also performed. The inhibition constant ($K_i$) for LPS, the dose at which LPS inhibits 50% of binding of [$^3$H] DPCPX ($IC_{50}$), and the lowest limit of detection for LPS in these membranes were determined. Results from these experiments are shown in Table 2 and in FIGS. 1, 2 and 3.

TABLE 2

Competition Experiments with LPS (0111:B4)
in Sheep and Hamster Brains and Feline PAECs

|  | $K_i$ (ng/ml) | $IC_{50}$ (ng/ml) | Detection Limit (ng/ml) |
|---|---|---|---|
| Sheep Brain | 48 | 100 | 1–10 |
| Hamster Brain | 147 | 377 | 0.1–1 |
| Cell Hypoxia | $k_{i1}$ 0.625, $K_{i2}$ 1000 | $IC_{50-1}$ 1, $IC_{50-2}$ 1750 | 1–10 |
| Cell Normoxia | $k_{i1}$ 0.267, $K_{i2}$ 607 | $IC_{50-1}$ 0.4, $IC_{50-2}$ 986 | 1–10 |

The sensitivity of the assay of the present invention is verified in competition experiments with known concentrations of endotoxin (1 pg/ml to 1 µg/ml) from 4 different species of LPS: *E. coli* 055:B5; *E. coli* 0111:B4, *Serratia marcescens*, and *Salmonella typhimurium* in saline or plasma in the presence of [$^3$H] DPCPX (0.2–0.5 nM) or [$^3$H] CCPA (0.2–0.5 nM). Radioligand binding data were analyzed by nonlinear regression analysis equipped with a statistical package. These data are then used as standard curves for the determination of endotoxin concentrations in samples.

Selectivity of the assay of the present invention is confirmed in competition experiments with known concentrations of a selective $A_2$ adenosine receptor agonist, 2-phenylaminoadenosine (CV1808)($10^{-12}$ to $10^{-4}$M), a thromboxane mimetic, U46619 ($10^{-12}$ to $10^{-4}$M), prostacyclin ($10^{-12}$ to $10^{-4}$ M), epinephrine ($10^{-12}$ to $10^{-4}$M), TNF-α ($10^{-12}$ to $10^{-4}$M), IL-1 ($10^{-12}$ to $10^{-4}$M) or (1→3)-β-D-Glucan from Alcaligenes faecalis var. Myxogenes IF013140 (Curdlan: Wako Pure Chemical Industries, Ltd. Osaka, Japan) (0–50 pg/ml) and gram positive bacteria, *Staphylococcus epidermis* or *Staphylococcus aureus* (1 pg/ml to 10 µg/ml)in saline in the presence of [$^3$H] DPCPX (0.2 to 0.5 nM) or [$^3$H] CCPA (0.2 to 0.5 nM). An endotoxin assay with LAL and chromogenic substrate (Endospecy, ES test: Seikagaku Corp., Tokyo) is performed according to manufacturer's protocol and used for comparison. Sensitivity and specificity of the radioligand binding assay for endotoxin or the LAL plus chromogenic substrate endotoxin assay are determined. The influences of interfering substances on the standard curves for endotoxin in the radioligand binding assay or LAL plus chromogenic substrate assay are also determined.

The present invention also provides kits for the detection of endotoxin in a sample and diagnosis of septicemia in an animal. In one embodiment, kits are provided for measuring the displacement of a detectably labeled $A_1$ adenosine receptor agent. In this embodiment, the kit comprises a source of $A_1$ adenosine receptors such as membranes containing $A_1$ adenosine receptors or purified $A_1$ adenosine receptors, a detectably labeled $A_1$ adenosine receptor agent, and endotoxin standards. In this embodiment, the kits may also comprise perchloric acid, dilution buffers such as phosphate buffered saline or Tris-HCl, non-pyrogenic filters, pipettes and test tubes. Alternatively, kits are provided for measuring endotoxin by RIA or ELISA. In this embodiment, the kits comprise a solid phase support coated with a first binding partner capable of binding endotoxin, a means for detecting endotoxin bound to the first binding partner, and endotoxin standards.

The following nonlimiting examples are provided to further illustrate the present invention.

EXAMPLES

Example 1

Preparation of $A_1$ Adenosine Receptors for Binding Experiments

Frozen sheep brain (Pel Freeze, Rodgers, Ark.) or hamster brain (Harlan Bioproducts, Indianapolis, Ind.) was thawed and homogenized in 10 volumes of cold (4° C.), 0.32 M sucrose. The homogenate was centrifuged at 1,000× g for 10 minutes to remove the nuclear fraction. The supernatant was centrifuged at 30,000× g for 30 minutes. The resulting pellet was resuspended in 10 ml water and left on ice for 30 minutes to obtain synaptosomal membranes. The suspension was then centrifuged at 48,000× g for 10 minutes and the membranes resuspended in 50 mM Tris-HCl (pH 7.4) at a concentration of 8 mg protein/ml, frozen in liquid nitrogen, and stored at −20° C. until binding assay.

Feline PAECs were grown to confluency in 75 mm$^2$ culture plates. The confluent cells were washed twice with KSP buffer (10 mM $KH_2PO_4$, 50 mM sucrose). The cells were scraped and suspended in KSP buffer at a concentration of 1×10$^6$ cells/ml in two conical centrifuge tubes. The tubes were centrifuged at 1000 g×2 minutes and the buffer discarded. The cells from one tube were then suspended in deoxygenated buffer (bubbled with $N_2$ gas for 10 minutes) and bubbled with $N_2$ gas for 30 seconds to insure hypoxic conditions. These cells were then incubated for 2 hours in this hypoxic buffer. Cells from the other tube were suspended in normal KSP buffer and incubated at 37° C. for 2 hours. At the end of incubation, cells were homogenized immediately for membrane preparation.

For membrane preparation, the cells were homogenized by sonication and centrifuged at 1000× g for 10 minutes. The supernatant was centrifuged again at 30,000× g for 30 minutes. The membrane fraction was reconstituted with Tris buffer for radioligand binding studies.

Example 2

Saturation Experiments

Binding of [$^3$H] DPCPX or [$^3$H] CCPA to membranes was carried out in an assay volume of 500 µl Tris-HCl, pH 7.4, $MgCl_2$ (10 mM) (for membranes from feline PAECs only) containing [$^3$H] DPCPX or [$^3$H] CCPA (0.01 to 4 nM). Nonspecific binding of [$^3$H] DPCPX or [$^3$H] CCPA was determined in the presence of R-PIA (100 µM) or theophylline (1 mM), respectively. To remove endogenous adenosine, adenosine deaminase was present in all binding assays at a concentration of 0.2 U/ml. Incubations were performed for 2 hours at room temperature for sheep and hamster brain membranes and 4° C. for feline PAEC membranes. Incubations were terminated by rapid removal of the incubation buffer by filtration through Whatman GF/B filters (Whatman Inc., Clifton, N.J.). The membrane bound radioactivity was measured by scintillation counting of the filter paper. To determine Kd, Bmax, and nonspecific binding in sheep and hamster brain and feline PAEC membranes, experiments are performed in duplicate.

Example 3

Competition Experiments

After determination of the Kd, Bmax and nonspecific binding of [$^3$H] DPCPX or [$^3$H] CCPA in membranes prepared from sheep and hamster brains and pulmonary arterial endothelial cells with and without hypoxia, competition experiments with known concentrations of endotoxin [LPS from *E. coli* 055:B5, *E. coli* 0111:B4, *Serratia marcescens*, and *Salmonella typhimurium;* 0.1 pg/ml–10 µg/ml in saline or plasma] were performed in the presence of [$^3$H] DPCPX or [$^3$H] CCPA (0.2–5 nM). Measurements of all samples (saline and plasma) were performed in duplicate.

Example 4

Statistical Analysis

Radioligand binding data are analyzed with the use of Graph Pad Prism by nonlinear regression analysis equipped with a statistical package. Data are expressed as mean±SEM. Hill plots and Schild plots are determined for each species of LPS in competition experiments and are used as standard curves for the determinations of the concentration of endotoxin in samples with unknown concentrations of endotoxin.

Example 5

Construction of an LPS Binding Curve

Saline is spiked with known concentrations of different species of LPS: *E. coli* 055:B5; *E. coli* 0111:B4, *Serratia marcescens*, and *Salmonella typhimurium* to produce a final concentration of 0, 1 pg/ml, 10 pg/ml, 100 pg/ml, 1 ng/ml, 10 ng/ml, 100 ng/ml, 1 µg/ml and 10 µg/ml LPS to construct standard curves for Radioligand Binding Endotoxin Assay, as described in Examples 2–4, or LAL plus Chromogenic Endotoxin Assay.

Blood from humans (5 ml) and animals (2 ml) is obtained in endotoxin-free syringes and anticoagulated test tubes containing endotoxin-free heparin (4 IU/ml) (Endo Tube ET, Chromogenix AB, Molndal, Sweden) and cooled in an ice bath immediately after obtaining the sample. The blood is centrifuged at 150× g for 10 minutes at 4° C. and 0.5–1.0 ml of the plasma layer is removed in a sterile manner using disposable pipettes (Steriltips, 1000 11L, Eppendorf, Darmstadt, Germany) and stored in LPS-free, sterile polypropylene tubes (Rorchen, 115271, 12.0/75 mm, Greiner Labortechnik, Frickenhausen, Germany) at –23° C. until assay. A sample of plasma is spiked with known concentrations of different species of LPS: *E. coli* 055:B5; *E. Coli* 0111:B4, *Serratia marcescens*, and *Salmonella typhimurium* to produce a final concentration of 0, 1 pg/ml, 10 pg/ml, 100 pg/ml, 1 ng/ml, 10 ng/ml, 100 ng/ml, 1 µg/ml and 10 µg/ml LPS and placed in an ice bath to construct standard curves for Radioligand Binding Endotoxin Assay or LAL, Chromogenic Endotoxin Assay. Perchloric acid precipitation of plasma to eliminate factors which interfere with LAL or radioligand binding assay is carried out as described by Obayashi, T. *J. Lab. Clin. Med.* 1984, 104:321–330. Two-tenths of a milliliter of 0.32 mol/L perchloric acid (PCA) is added to 0.1 ml sample in an ice bath, and the mixture is incubated at 37° C. for 20 minutes. The denatured material is precipitated by centrifugation at 3000 rpm for 15 minutes, and the supernatant is neutralized with an equal volume of 0.18 M NaOH.

Example 6

Determination of Endotoxemia in Samples of Affected Individuals

Blood from humans (5 ml) and animals (2 ml) suspected of having septicemia is collected in endotoxin-free syringes and anticoagulated test tubes containing endotoxin-free heparin (4 IU/ml) (Endo Tube ET, Chromogenix AB, Molndal, Sweden) and cooled in an ice bath immediately after obtaining the sample. The blood is centrifuged at 150× g for 10 minutes at 4° C. and 0.5–1.0 ml of the plasma layer is removed in a sterile manner using disposable pipettes (Steriltips, 1000 Aisle, Eppendorf, Darmstadt, Germany) and stored in LPS-free, sterile polypropylene tubes (Rorchen, 115271, 12.0/75 mm, Greiner labortechnik, Frickenhausen, Germany) at –23° C. until assayed for the presence of endotoxin according to the methods described herein.

What is claimed:

1. A method of determining endotoxin levels in a sample comprising:
   (a) providing an agent which binds to $A_1$ adenosine receptors;
   (b) contacting an $A_1$ adenosine receptor with a sample in the resence of said agent of step (a) so that any enclotoxin in the sample inhibits binding of said agent of step (a) to the $A_1$ adenosine receptor;
   (c) measuring any bound agent of step (a); and
   (d) determining endotoxin levels in the sample by comparison to a standard curve derived by measuring amounts of agent of step (a) bound to $A_1$ adenosine receptors in the presence of known concentrations of a known endotoxin.

2. The method of claim 1 wherein the agent of step (a) is detectably labeled.

3. The method of claim 1 wherein the $A_1$ adenosine receptor is immobilized to a solid phase support.

4. A method for determining endotoxin levels in a sample comprising:
   (a) coating a solid phase support with an antibody to $A_1$ adenosine receptors;
   (b) contacting the solid phase support with $A_1$ adenosine receptors which bind to the antibody coated on the solid phase support;
   (c) contacting the solid phase support of step (b) with a sample containing endotoxin in the presence of a detectably labeled agent which binds $A_1$ adenosine receptors so that the endotoxin inhibits binding of the detectably labeled agent to the $A_1$ adenosine receptors bound on the solid phase support;
   (d) measuring any labeled bound agent of step (c); and
   (e) determining endotoxin levels in the sample by comparison to a standard curve derived by measuring amounts of bound agent of step (c) in the presence of known concentrations of a known endotoxin.

* * * * *